United States Patent [19]

Awaya et al.

[11] Patent Number: 5,352,665
[45] Date of Patent: Oct. 4, 1994

[54] METHOD OF TREATING DISEASE CAUSED BY THE INFECTION OF VIRUS

[75] Inventors: Akira Awaya, Yokohama; Hisashi Kobayashi, Mobara; Yusaku Ishizuka, Yokohama; Hayao Abe, Mobara, all of Japan

[73] Assignee: Mitsui Toatsu Chemicals, Incorporated, Tokyo, Japan

[21] Appl. No.: 91,745

[22] Filed: Jul. 15, 1993

Related U.S. Application Data

[63] Continuation of Ser. No. 827,918, Jan. 31, 1992, abandoned, which is a continuation of Ser. No. 415,332, filed as PCT/JP88/01183, Nov. 24, 1988, abandoned.

[30] Foreign Application Priority Data

Nov. 24, 1987 [JP] Japan .................. 62-294200

[51] Int. Cl.$^5$ ................................... C07K 7/06
[52] U.S. Cl. ................................ 514/15; 530/328
[58] Field of Search .................... 514/15; 530/328

[56] References Cited

U.S. PATENT DOCUMENTS 4,098,777 7/1978 Veber et al. ............. 260/112.5 R

FOREIGN PATENT DOCUMENTS 0043247  1/1982 European Pat. Off. .
0232435  8/1987 European Pat. Off. .
58-52225 3/1983 Japan ......................... 514/15

OTHER PUBLICATIONS

J. Pharm. Clin., vol. 5, No. 2, 1986, pp. 169–178; Werner "Place des immunomodulateurs dans le traitment des maladies virales" Translation of relevant parts of J. Pharm. Clin.
Bach, Thymulin (FTS-Zn), Clinics in Immunology and Allergy, vol. 3, No. 1, Feb. 1, 1983.

Primary Examiner—Lester L. Lee
Attorney, Agent, or Firm—Nixon & Vanderhye

[57] ABSTRACT

A medicament for prevention and remedy of diseases caused by the infection of viruses is disclosed, which is characterized by containing as an effective ingredient thereof a nonapeptide having the following amino acid configuration:

pGlu-Ala-Lys-Ser-Gln-Gly-Gly-Ser-Asn or an ester and an amide at the carboxyl group of the C-terminal of the asparagine or a pharmacologically acceptable salt thereof.

8 Claims, No Drawings

METHOD OF TREATING DISEASE CAUSED BY THE INFECTION OF VIRUS

This is a continuation of application Ser. No. 07/827,918, filed Jan. 31, 1992, and now abandoned which is a continuation of Ser. No. 07/415,332, filed as PCT/JP88/01183, Nov. 24, 1988, now abandoned.

INDUSTRIAL APPLICABILITY

The present invention relates to a new medicament for human or animals. More particularly, the present invention relates to a medicament for prevention and remedy of diseases caused by the infection of various virus such as virus attacking skin, cornea, sexual organs and nervous system, virus attacking digestive organs and virus attacking respiratory organs. The present invention relates to a new medicament capable of recovering the normal function of hosts infected with various virus from their symptoms such as suppression of immunity or outbreak of diabetes accompanied with the infection of virus.

BACKGROUND ART

The development of medicaments for remedy and prevention of diseases caused by the infection of virus lags behind the case of infection diseases of human and animals caused by bacilli or protozoa. Some of viruses as etiological matter are weakened in toxicity or inactivated to develop vaccines for practical use, but the number of such vaccines is not many.

In more specific examples, medicaments except vaccines, for example, chemotherapeutic agents are scarcely utilized as medicaments for prevention and remedy of infection diseases caused by REO virus attacking digestive and respiratory organs, rotavirus, orbivirus and coronavirus attacking digestive organs, or adenovirus, rhinovirus, influenza virus, parainfluenza virus, etc. attacking respiratory organs. The use of a biophylactic stimulant or the like is thinkable which is different in principle of effect and mechanism from chemotherapeutic agents. However, there is scarcely seen an example of such application. In recent years, studies on various peptides were reported as being effective to various diseases caused by viruses. In Japanese Laid-open Patent Appln. No. Sho. 59-51247 and Japanese Laid-open Patent Appln. No. Sho. 59-98049, for example, there are described syntheses of various new peptides and the effect of these synthesized peptides to animal models infected with colitis Germs and herpes virus. In Japanese Laid-open Patent Appln. No. Sho. 60-104019, there is disclosed that a certain kind of acylpeptides containing D-amino acids possesses an effect of increasing survival rate on mice infected with influenza virus or herpes virus. In Japanese Laid-open Patent Appln. No. Sho. 57-192349, there is disclosed that six kinds of tripeptides consisting of the three amino acids; leucine, alanine and phenylalanine exhibits an anti-virus effect on mice infected with hepatitis virus MHV$_3$. Further, Japanese Laid-open Patent Appln. No. Sho. 58-92642 gives a disclosure that a basic pentapeptide having an amino acid configulation of Arg-Lys-Asp-Val-Tyr is useful for the remedy of diseases caused by the infection of virus.

Nature 321, 439–441 (1986) and ibid. 441–443 (1986) disclose that a certain kind of synthetic nonapeptides exhibits an anti-herpes-virus effect based on its enzyme-inhibitory effect on ribonucleotide reductase of herpes virus.

The majority of the peptides disclosed in these known literatures were synthesized and are novel. However, these are merely reported as above and have not yet been put into practice as medicaments for prevention and remedy of diseases caused by virus. Moreover, no substantial study have been made for the majority of these synthetic peptides on any toxicity, side-effect, antigenicity and anaphylactic shock in case of using these as medicaments for human and animals.

DISCLOSURE OF THE INVENTION

With a view to developing a medicament which is different from chemotherapeutic agents and is capable of enhancing the defending ability inherently existing in living body, the present inventors have made extensive researches on various peptides of natural origin higher in safety to find out a substance useful as a medicament for prevention and remedy of infection diseases caused by REO virus, rotavirus and the like. As a result of the researches, it has now been found that a nonapeptide known as the factor of thymic serum (Facteur thymique serique which will be referred to hereinafter simply as FTS) and derivatives or salts thereof are effective to prevent completely suppression of immunity in mice infected with various viruses such as REO virus, to recover the infected mice to the normal state and to prevent outbreak of diabetes such as increase in blood sugar.

The present invention has been accomplished on the basis of the above finding. One of the present inventors previously found that a nonapeptide known as FTS was suitable as a therapeutic agent for multiple sclerosis, Guillain-Barre syndrome, inflammatory neuritis, polyneuritis and other various diseases accompanying immunodeficiency such as immunological demyelinating diseases, and provided such therapeutic agents (Japanese Laid-open Patent Appln. No. Sho. 58-52225). The present invention provides a medicament for prevention and remedy of various diseases and disorders caused by the infection of virus.

In accordance with the present invention, there is provided a medicament for prevention and remedy of diseases caused by the infection of virus, characterized by containing as an effective ingredient thereof a nonapeptide having the following amino acid configuration:

pGlu-Ala-Lys-Ser-Gln-Gly-Gly-Ser-Asn or an ester and an amide at the carboxyl group of the C-terminal of the asparagine or a pharmacologically acceptable salt thereof.

According to the present invention, there is provided a medicament for prevention and remedy of diseases and various disorders caused by the infection of various viruses such as adenovirus, enteric adenovirus, influenza virus, parainfluenza virus, orbuvirus, coronavirus, encephalomyocarditis virus, enterovirus, ECHO virus (enteric cytopathogenic human orphan virus), coxsackie A group virus, coxsackie B group virus, cytomegalovirus, varicella-zoster virus, papilloma virus, baculovirus, picorna virus, rubella virus, mumps virus, encephalitis virus, SSPE virus, polio virus, measles virus, stomatitis virus, hepatitis virus, rhinovirus, REO virus, rotavirus, vaccinia virus, pig Oasky's disease virus, and various retro viruses such as HTLV-I, II and III [HTLV-III is also called HIV (human immunodeficiency virus)], SIV (monkey) and FIV (cat).

The nonapeptide used in the present invention can be prepared without difficulty according to a liquid phase or solid phase peptide synthetic method conventionally employed for the synthesis of usual peptides (Concerning these methods, please refer to Japanese Laid-open Patent Appln. No. Sho. 54-16425 and U.S. Pat. No. 4,301,065). Alternatively, the nonapeptide can be prepared also by a genotechnological or cell technological procedure.

The esters at the carboxyl group of C-terminal of the asparagine in the-nonapeptide used in the present invention are those of the carboxylic acid pharmacologically acceptable and examples of such esters include methyl ester, ethyl ester, propyl ester, isopropyl ester, n-butyl ester, isobutyl ester, tert-butyl ester, n-pentyl ester, isopentyl ester, neopentyl ester, tert-pentyl ester, n-hexyl ester, sec-hexyl ester, heptyl ester, octyl ester, sec-octyl ester, tert-octyl ester, nonyl ester, decyl ester, undecyl ester, dodecyl ester, tridecyl ester, tetradecyl ester, hexadecyl ester, octadecyl ester, nonadecyl ester, eicocyl ester, cyclopentyl ester, cyclohexyl ester, cycloheptyl ester, cyclooctyl ester, allyl ester, isopropenyl ester, benzyl ester, o-, m- or p-chlorobenzyl ester, o-, m- or p-fluorobenzyl ester, o-, m- or p-bromobenzyl ester, o-, m- or p-iodobenzyl ester, o-, m- or p-methylbenzyl ester, o-, m- or p-ethylbenzyl ester, o-, m- or pisopropylbenzyl ester, cinnamyl ester, aminoethyl ester, o-, m- or p-aminobenzyl ester, o-, m- or p-nitrobenzyl ester, o-, m- or p-methoxybenzyl ester, o-, m- or pethoxybenzyl ester, o-, m- or p-aminophenetyl ester, α-furfuryl ester, α-thienylmethyl ester, α-pyridylmethyl ester, α-pyridylethyl ester, piperidinomethyl ester, α-piperidylmethyl ester, morpholinomethyl ester, α-morpholinylmethyl ester. The amides at the carboxyl group of C-terminal of the asparagine in the nonapeptide used in the present invention are those of carboxylic acid pharmacologically acceptable and examples of such amides include amide itself, methylamide, ethylamide, propylamide, isopropylamide, n-butylamide, isobutylamide, tert-butylamide, n-pentylamide, isopentylamide, neopentylamide, tert-pentylamide, n-hexylamide, sec-hexylamide, heptylamide, octylamide, sec-octylamide, tertoctylamide, nonylamide, decylamide, undecylamide, dodecylamide, tridecylamide, tetradecylamide, hexadecylamide, octadecylamide, nonadecylamide, eicosylamide, cyclopentylamide, cyclohexylamide, cycloheptylamide, cyclooctylamide, allylamide, isopropenylamide, benzylamide, o-, m- or p-chlorobenzylamide, o-, m- or p-fluorobenzylamide, o-, m- or p-bromobenzylamide, o-, m- or p-iodobenzylamide, o-, m- or p-methylbenzylamide, o-, m- or p-ethylbenzylamide, o-, m- or p-isopropylbenzylamide, cinnamylamide, aminoethylamide, o-, m- or p-aminobenzylamide, o-, m- or p-nitrobenzylamide, o-, m- or p-methoxybenzylamide, o-, m- or p-ethoxybenzylamide, o-, m- or p-aminophenethylamide, α-furfurylamide, α-thienylmethylamide, α-pyridylmethylamide, α-pyridylethylamide, piperidinomethylamide, α-piperidylmethylamide, morpholinoethylamide, α-morpholinylmethylamide, methoxycarbonyl-(α-mercapto-methyl)methylamide and ethoxycarbonyl-(α-mercapto-methyl)methylamide.

The above mentioned pharmacologically acceptable salts include acid-additions salts at the amino group of the nonapeptide and salts with bases at the carboxylic acid of the nonapeptide. The acid-addition salts include those with organic acids and inorganic acids. Illustrative of these salts are, for example, salts with carboxylic acids such as formic acid, acetic acid, propionic acid, trifluoroacetic acid, tartaric acid, fumaric acid, malic acid, maleic acid, oxalic acid and naphthoic acid and salts with sulfonic acids such as methanesulfonic acid, p-toluenesulfonic acid and naphthalenesulfonic acid as well as salts with inorganic acids such as hydrochloric acid, sulfuric acid, nitric acid and phosphoric acid.

The above mentioned salts with bases include salts with inorganic bases, such as alkali metal salts, alkaline earth metal salts and ammonium salts as well as salts with organic bases, i.e. salts with amines. Illustrative of these salts are lithium salt, sodium salt, potassium salt, calcium salt, ammonium salt, triethyl amine salt, ethanolamine salt, tris salt and dicyclohexylamine salt.

The medicament concerned with the present invention for prevention and remedy of diseases caused by the infection of viruses such as mumps virus, REO virus, enterovirus, cytomegalovirus, rotavirus, orbivirus, coronavirus, adenovirus, rhinovirus and influenza virus can be prepared in a usual conventional pharmaceutical manner according to the type of the medicaments. An effective ingredient selected from the nonapeptide, an ester, an amide, and a salt thereof is processed properly with a pharmacologically acceptable carrier, excipient or diluent to a suitable type of medicament. The medicament can be made in any of the various types suitable for the route of administration such as external application, oral administration, non-oral administration, etc.

The effect of the preventive and therapeutic medicament of the present invention as an agent for curing the state of suppressing immunity caused by the infection of virus or bacilli or various stress is confirmed by the experiments as described below.

NC mice or BALB/c mice infected with pig Oasky's disease virus (Yamagata S81 strain) by subcutaneous innoculation. A given amount of a nonapeptide known as FTS was administered to the mice only the precedent day of the infection, or alternatively, 2-3 times before and after the infection, and survival or death of the mice, symptom of nervous system and change in skin by the disease were observed. In a group of mice to which the nonapeptide was administered, an average day of death is extended in each group of mice innoculated with a different factor of the virus. The symptom of the nervous system and the skin by disease were also obviously improved. It is considered that macrophage or the function of NK cells or the like against virus is increased at the initial stage of the infection of virus to prevent invasion of virus into body. Furthermore, newly born NC mice, newly born ICR mice, etc. were infected with REO virus (respiratory enteric orphan virus) type II by intraperitoneal innoculation.

Two weeks after the infection of $10^5$ PFU REO virus, sheep red blood cells (referred to hereinafter simply as SRBC) was intraperitoneally administered and 4 days after the administration, the number of hemolysis plaques was measured by way of Jerne plaque assay as a production amount of antibody-forming cells against SRBC. The number of hemolysis plaques was 15±2 per $10^6$ spleen cells in a group not infected with REO virus, while that was 2.8±1.6 in an infected group, thus showing a remarkable immunity inhibitory state. In compliance with this, atrophy of thymus and decrease in the number of thymic cortex lymphocytes were observed.

On the other hand, the effective ingredient of this invention dissolved in physiological saline was administered in an amount of 10 μg/mouse simultaneously with SRBC to mice, and 4 days after the administration, the number of hemolysis plaques was measured whereupon the number was 22±5. In a Group as control to which lipopolysaccharide (LPS) was administered in an amount of 5 μg/mouse, the number was 0.3±0.4, thus showing no therapeutic effect. In a group to which muramyl dipeptide was administered in an amount of 20 μg/mouse together with Freund incomplete adjuvant, the number of hemolysis plaques was 11±2. It follows therefore that the effective ingredient of the medicament of this invention showed a therapeutic effect 2 times higher than the above case. In the other experiments for the infection of $10^5$ PFU/mouse REO virus to check dose response, a Group to which the effective ingredient of the medicament of this invention were administered showed the number of hemolysis plaques as great as 41±7.

Similarly, newly born ICR mice were innoculated with $10^4$ PFU REO virus and the number of hemolysis plaques was measured with the same protocol whereupon a group to which the effective ingredient of the medicament of this invention was administered in an amount of 10 μg/mouse recovered the immunological response capacity to the same level as that of the immunological response capacity of untreated mice 18 days after the infection of virus.

Further, 4 weeks after the infection of newly born NC mice with $10^4$ PFU REO virus, the effective ingredient of the medicament of this invention was administered to the mice in an amount of 10 μg/mouse and a plaque assay was carried out whereupon the immune function was recovered from the immunity inhibitory state to almost the normal level.

Next, the effective ingredient of the medicament of this invention was administered to newly born ICR mice 14 days after being infected with $10^4$ PFU REO virus, and 4 days after the administration, any disorder of glucose tolerance was measured whereupon the blood sugar level of the mice was recovered to the normal level in a group of the mice to which the effective ingredient was administered and the percentage of mice to be deemed as diabetes was obviously decreased.

In a similar measurement of the blood sugar level with a similar protocol was carried out for newly born NC mice infected with $10^5$ PFU/mouse of REO virus whereupon the blood sugar level was obviously restored to the normal level in a group of the mice to which the effective ingredient of the medicament of this invention was administered and no mice to be deemed as diabetes was found in a group of the mice to which the effective ingredient was administered in an amount of 10 μg/mouse. The total number of splenic lymphocytes and macrophages of new-born ICR mice was increased by the infection of the mice with REO virus. When the effective ingredient of the medicament of this invention was administered to the mice 2 weeks and 4 weeks after the infection, however, it was made clear that the total number of the monocytes was decreased to the level of untreated mice. It was manifested therefore that the effective ingredient of the medicament of this invention possesses effects of recovering disorder of immunity or immunity-inhibitory state of animals caused by the infection of virus or the like and of preventing increase in the level of blood sugar.

In an experiment for the infection of cattle with rotavirus (Nebraska strain) and monkey rotavirus SA 11 strain, it has been found that the nonapeptide is effective for inhibition of death/extension of life span and for prevention and remedy of infection diseases. It has also been found that the conjoint use of the nonapeptide with a rotavirus vaccine serves to enhance the vaccination effect.

The nonapeptide in the coexistence of human T lymphocytes infected with HTLV-I and HTLV-II and of MT-4 infected with HTLV-III exhibits an inhibitory action to destroy of cells, a cells-stabilizing action and an inhibitory action to propagation of virus. Thus, FTS is considered to be applicable as a preventive and therapeutic medicament for human T-cell leukemia, HTLV-I-associated myelopathy (HAM), a typical T cell haivy cell leukemia and acquired immunodeficiency syndrome (AIDS) and the like diseases. In accordance with the present invention, there is provided a medicament for prevention and remedy of diseases and various disorders caused by the infection of various viruses such as adenovirus, enteric adenovirus, influenza virus, parainfluenza virus, orbivirus, coronavirus, encephalomyocarditis virus, enterovirus, ECHO virus, coxsackie A group virus, coxsackie B group virus, cytomegalovirus, varicellazoster virus, papilloma virus, baculovirus, picorna virus, rubella virus, mumps virus, encephalitis virus, SSPE virus, polio virus, measles virus, stomatitis virus, hepatitis virus, rhinovirus, REO virus, rotavirus, vaccinia virus, pig Oasky's disease virus, and various retro viruses such as HTLV-I, II and III [HTLV-III is also called HIV (human immunodeficiency virus)], SIV (monkey) and FIV (cat).

To check any toxicity of the effective ingredient of the medicament of this invention, 100 mg/kg of the effective ingredient was subcutaneously administered every day for consecutive 14 days to mice whereupon no abnormal symptom was found by external check. Further, 30 mg/kg of the effective ingredient was subcutaneously administered to rats for consecutive 21 days whereupon no abnormal symptom was found in external behavior observation and biochemical diagnosis of sera and in a result of pathological anatomy. Thus, the medicament of the present invention is a safe medicament of extremely low toxicity and can be administered for a long period of time.

As animals to which the medicament of this invention can be administered, there can be mentioned, for example, human, domestic animals such as cattle, horse, pig, sheep, goat, rabbit, dog and cat, mammalian kept in zoo or the like such as lion, elephant, giraffe, bear, gorilla, monkey and chimpanzee, various test animals such as mouse, rat, guinea pig and the like, domestic fowls such as fowl, and pets such as birds, reptiles, amphibia and fishes. The dose of the medicament is usually 0.1 μg—500 mg/day for 1 kg body weight of these animals. The medicament in these doses may be administered, for example, in 1–6 portions in a day. The dose may properly be increased or decreased according to ages, symptoms, etc. of the objects to be administered. No limitation exists in the route of administration of the medicament, but it may be administered by intravenous, intramuscular intracutaneous and subcutaneous injection. The medicament can be processed to an ointment which is applied to eyes, oral cavity, nasal cavity and skin. The medicament can be administered in the form of a suppository, a jelly, eye drops, nasal drops, preparations absorbable in nasal or oral cavity, an aerosol, a spray and oral preparations. In order to prevent the effective ingredient from rapid decomposition or inactivation in the living body, the effective ingredient may be processed with appropriate pharmaceutical ingredients, for example, alcoholic, oily or fatty physiologically harmless solid or liquid materials such as lecithin or a suspension liposome thereof to medical preparations in which the activity is maintained for a long period of time. The medicament of the present invention can be administered together with various other medicines, for example, chemotherapeutic agents possessing anti-viral activity, antibiotics, vaccines against individual viruses, antibodies or biological response modifiers such as immunostimulants, or alternatively may be incorporated with these as a combination agent to enhance clinical effects.

The present invention will now be illustrated in more detail by way of examples and experimental examples, but the present invention is not limited by these examples.

EXAMPLE 1 A vial preparation for injection

In a distilled water was dissolved 1 mg of FTS-$CH_3COOH.2H_2O$ (prepared by Mitsui Seiyaku Kogyo KK) and the solution was subjected to sterilizing filtration, charged into a vial and then subjected to lyophilization.

EXAMPLE 2 An ampoule preparation for injection

In physiological saline was dissolved 5 mg of FTS-$CH_3COOH.2H_2O$ (prepared by Mitsui Seiyaku Kogyo KK) and the solution was subjected to sterilizing filtration and charged into an ampoule.

EXAMPLE 3 An injection preparation for subcutaneous injection

In a 2% carboxymethylcellulose PBS (physiological saline buffered with a phosphate) was suspended 2 mg per unit dose of FTS.$CH_3COOH.2H_2O$ (prepared by Mitsui Seiyaku Kogyo KK). The suspension was mixed with Lipomal comprising soybean phosphatide (prepared by Huhtamaki Oy/Leiras Pharmaceuticals Co.)or Intralipid (prepared by Cutter Laboratories) as an oil-in-water type emulsion for intravenous injection. In case of using Lipomal, the PBS solution dissolving FTS was mixed with an equiamount of Lipomal. In case of using Intralipid, 2.5 ml of the PBS solution dissolving FTS was mixed with 0.1 ml of Tween 80 (prepared by Sigma Chemicals Inc.) and 4.6 ml of Intralipid.

EXAMPLE 4 A liposome preparation

There are 3 kinds of liposome preparations which are different in electric charge from one another. The liposome preparations are classified by their structures into 4 kinds.

There are 3 kinds of electric charge: neutral, positive and negative. In view of the structure, there are known 4 kinds; a multilaminar liposome (MLV, multilamellar vesicle), a small unilaminar liposome (SUV, small unilamellar vesicle), a large unilaminar liposome (LUV, large unilamellar vesicle) and one having a structure similar to LUV but having several lamellae (REV, reverse-phase evaporation vesicle).

(1) A neutral electric charge liposome enclosing FTS:

A phospholipid such as phosphatidylcholine or sphingomyelin and a solution of cholesterol in chloroform were mixed in a mole ratio of 2:1, 4:1 or 1:1 and the solvent was once removed from the mixture by distillation under reduced pressure. A solution of 1/100–1/1000 equivalent of FTS in PBS (physiological saline buffered with a phosphate) was added to the mixture and the whole was well mixed by the aid of a Vortex mixer whereby MLV was obtained.

This was then subjected to an ultrasonic treatment above a phase transition temperature (Tc) of the phospholipid whereby SUV was obtained.

An aqueous solution of calcium chloride was added to the resultant SUV and the mixture was incubated for 1 hour at 37° C. to effect hybridization. EDTA was then added and the mixture was incubated for 30 minutes at 37° C. to eliminate $Ca^{++}$ whereby LUV was obtained.

The method for preparing REV is as follows: After removing the solvent from a chloroform solution of the lipid by distillation under reduced pressure, a proper amount of diethyl ether is added to dissolve the lipid satisfactorily. A PBS solution of FTS is added to the solution and the mixture is subjected to an ultrasonic treatment to obtain a homogeneous uniphase solution. After concentrating the resultant solution under reduced pressure at room temperature, the PBS solution is added to the residue and the mixture was mixed well by the aid of a Vortex mixer to obtain REV.

(2) A positively charged liposome enclosing FTS:

Except that the constituents of the lipid are different, the method for preparing the liposome is same as that in case of the above mentioned neutral electric charge liposome.

A phospholipid such as phosphatidylcholine or sphingomyelin, cholesterol, and a positively charged higher aliphatic amine such as stearylamine were mixed together in a molar ratio of 7:2:1 or 4:1:1 to form a lipid ingredient, and FTS was enclosed in a similar manner.

(3) A negatively charged liposome enclosing FTS:

A phospholipid such as phosphatidylchlorine or sphingomyelin, cholesterol, and a negatively charged higher aliphatic ester such as dicetyl phosphate or sulfatide were mixed together in a molar ratio of 7:2:1 or 4:1:1 to form a lipid ingredient, and FTS was enclosed in a similar manner.

EXAMPLE 5 An ointment

In purified water was dissolved 2 mg of FTS.$CH_3COOH.2H_2O$ (prepared by Mitsui Seiyaku Kogyo KK). Next, 25 g of white vaseline, 20 g of stearyl alcohol, 4 g of HCO-60 and 1 g of glycerol monostearate were weighed and mixed. A previously prepared aqueous solution (containing FTS) of 12 g of propylene glycol, 0.1 g of methyl p-hydroxybenzoate and 0.1 g of propyl p-hydroxybenzoate was added to the mixture and the whole was thoroughly blended to form an emulsion which was then mixed until it was cooled and solidified.

EXAMPLE 6 A suppository

In a hard fat previously warmed was dispersed 10 mg of FTS.$CH_3COOH.2H_2O$ (prepared by Mitsui Seiyaku Kogyo KK). The total amount was adjusted to 2 g.

EXAMPLE 7 A capsule for nasal use

In 29.95 mg of miglyol 812 neutral oil (Dynamite Nobel Co.) was dissolved under a sterilizing condition 0.05 mg of FTS. This solution was charged into a conventional unit-dose capsule which was treated with an applying device just before the use.

EXAMPLE 8 Nasal drops

In distilled water were dissolved at room temperature sodium dihydrogen phosphate, disodium hydrogen phosphate, sodium chloride and EDTA-disodium salt in amounts shown below. FTS was dissolved in this solution which was then filtered through a membrane filter.

| FTS | 0.10 mg |
|---|---|
| Sodium monohydrogen phosphate 2H₂O | 0.30 mg |
| Sodium dihydrogen phosphate 12H₂O | 10.10 mg |
| Benzalconium chloride | 0.10 mg |
| Ethylenediamine tetraacetic acid disodium salt (EDTA) | 0.50 mg |
| Sodium chloride | 4.50 mg |
| Distilled water | 987.60 mg |
| pH value | 5.0 ± 0.3 |

EXAMPLE 9 A nasal spray preparation

In hydroxypropylcellulose or hydroxypropylmethylcellulose was suspended FTS·CH$_3$COOH·2H$_2$O (prepared by Mitsui Seiyaku Kogyo KK). The suspension was processed to a spray preparation by the aid of a spray-preparing machine.

Given below are examples for pharmacological experiments and Toxicity experiments concerning the medicament of this invention.

EXPERIMENTAL EXAMPLE 1

New-born NC mice were infected with $10^5$ PFU REO virus, and 4 weeks after the infection, the mice were inoculated with sheep red blood cells to check immune function. The number of hemolysis plaques was 38±8 per $10^6$ spleen cells in a control group, while no hemolysis plaque was detected in more than half of the infected mice and the number of hemolysis plaques was wholly decreased to 8±6, showing strong disorder of immunity.

In a pathomorphological examination of the mice showing immune inhibition, atrophy of thymus and decrease in the number of thymic cortex lymphocytes were observed in the mice.

Next, recovery of the immune function by immunity-enhancing substance was examined, using new-born mice infected with REO virus type II. Two weeks after the infection of the mice with the virus, sheep red blood cells were administered to the mice, and 4 days after the administration, Jerne plaque assay was carried out to measure the number of hemolysis plaques. The number was 15±2 in a group of the mice not infected and was 2.8±1.6 in a group of the infected mice. Although coliform bacillus (E. coli 055:B5) and lipopolysaccharide (LPS manufactured by Sigma Co.) were administered together with sheep red blood cells to the infected mice, no therapeutic effect was observed. In case of the mice to which Freund incomplete adjuvant and muramyl dipeptide (MDP prepared by Sigma Co.) (20 μg/mouse) had been administered together with sheep red blood cells, the number of hemolysis plaques of 11±2 was detected, thus showing a therapeutic effect. In a group of the mice to which FTS (10 μg/mouse) had been administered, however, the number was 22±5, thus showing a therapeutic effect of 2 times as much as MDP. This recovery of the function of immune inhibition is tabulated as follows:

| Mouse strain | Infection of REO virus | Immunity-enhancing substance | Number of mice | PFC/$10^6$ spleen cells |
|---|---|---|---|---|
| NC | − | − | 32 | 15 ± 2 |
|  | + | − | 12 | 2.8 ± 1.6 |
|  | + | LPS 5 μg/mouse | 7 | 0.3 ± 0.4 |
|  | + | MDP 20 μg/mouse | 5 | 11 ± 2 |
|  | + | FTS 10 μg/mouse | 5 | 22 ± 5 |

Recovery of the function in case of using immunity-enhancing substances

Mice infected with virus was immunized at the same time with SRBC and an immunostimulant, and 4 days after the immunization, the number of hemolysis plaques was measured by Jerne plaque assay.

EXPERIMENTAL EXAMPLE 2

FTS in an amount of 10 μg/mouse was administered to mice infected with REO virus, and 18 days after the administration, inhibition of immunity and recovery of its function were observed by way of Jerne plaque assay.

Mouse: ICR new-born mouse
Virus: REO virus type II, innoculation 1 × $10^4$ PFU/mouse

| Infection of virus | Administration of FTS | PFC/$10^6$ splenic cells |
|---|---|---|
| − | − | 372 ± 44 (7 mice) |
| + | − | 26 ± 9 (5 mice) |
| + | + | 334 ± 26 (5 mice) |

EXPERIMENTAL EXAMPLE 3

New-born ICR mice were infected with $10^4$ PFU REO virus type II. About 4 weeks after the infection, FTS was administered in an amount of 10 μg, 1 μg or 0.1 μg to the mice, and inhibition of immunity and recovery of its function were observed respectively.

| Infection of virus | Administration of medicament | PFC/$10^6$ splenic cells |
|---|---|---|
| − | − | 299 ± 13 (11 mice) |
| + | − | 17 ± 4 (13 mice) |
| + | FTS 10 μg | 253 ± 22 (7 mice) |
| + | FTS 1 μg | 171 ± 21 (7 mice) |
| + | FTS 0.1 μg | 31 ± 13 (6 mice) |

EXPERIMENTAL EXAMPLE 4

After mice being infected with REO virus, 10 μg 1 μg or 0.1 μg of FTS was administered to the mice. After 18 days, inhibition of immunity and recovery of its function were observed by way of Jerne plaque assay.

Mouse: NC new-born mouse
Virus: REO virus type II, innoculation 1 × $10^5$ PFU/mouse

| Infection of virus | Administration of FTS | PFC/$10^6$ splenic cells |
|---|---|---|
| − | − | 15 ± 2 (32 mice) |
| + | 10 μg | 41 ± 7 (7 mice) |
| + | 1 μg | 41 ± 13 (5 mice) |
| + | 0.1 μg | 19 ± 6 (4 mice) |

| Infection of virus | Administration of FTS | PFC/10⁶ splenic cells |
|---|---|---|
| + | 0 μg | 2.8 ± 1.6 (12 mice) |

EXPERIMENTAL EXAMPLE 5

Diabetes caused by REO virus and recovery of function by FTS.

New-born ICR mice were infected with $10^4$ PFU REO virus type II. About 2 weeks after the infection, 10, 1 and 0.1 μg of FTS was administered to the mice, and 4 days after the administration, disorder of glucose tolerance of the mice was measured. Blood sugar glucose was measured with the aid of a glucose assay kit manufactured by Sigma Co. (the glucose oxidase method).

| Infection of virus | Administration of medicament | Blood sugar mg/dl | Diabetes % |
|---|---|---|---|
| − | −(22 mice) | 144 ± 16 | 0 |
| + | −(12 mice) | 178 ± 48 | 42 |
| + | FTS 10 μg (7 mice) | 144 ± 21 | 14 |
| + | FTS 1 μg (7 mice) | 167 ± 17 | 43 |
| + | FTS 0.1 μg (6 mice) | 180 ± 46 | 33 |

Mice having a blood sugar value exceeding 2SD of the blood sugar value (144±16) of control, i.e. a value greater than 176 mg/dl as an abnormal value were regarded as diabetes. As some of the mice infected with REO virus show a low level of blood sugar, FTS in a small dose does not seem to be strong in it effect. In case of the administration of 10 μg FTS, however, the blood sugar value was decreased to the normal value to reduce the diabetes percentage apparently.

EXPERIMENTAL EXAMPLE 6

New-born NC mice were infected with $10^5$ PFU REO virus type II. About 2 weeks after the infection, 10 μg, 1 μg or 0.1 μg of FTS was administered to the mice, and 4 days after the administration, disorder of glucose tolerance of the mice was measured.

| Infection of virus | Administration of medicament | Blood sugar mg/dl | Diabetes % |
|---|---|---|---|
| − | −(10 mice) | 193 ± 12 | 0 |
| + | −(10 mice) | 367 ± 36 | 90 |
| + | FTS 10 μg (5 mice) | 198 ± 11 | 0 |
| + | FTS 1 μg (5 mice) | 226 ± 6 | 20 |
| + | FTS 0.1 μg (4 mice) | 404 ± 63 | 100 |

In cases of FTS being 10 μg and 1 μg, apparent decrease of the blood sugar values to the normal value was observed. Thus, obvious reduction in diabetes percentage was shown in the case of NC mouse as compared with the case of ICR mouse.

EXPERIMENTAL EXAMPLE 7

Increase in the number of splenic lymphocytes and macrophages caused by the infection of virus and inhibition of increase in the number of splenic cells by FTS

TABLE A

| Infection of virus | Administration of FTS 10 μg | Splenic cells/(mice) ×10⁷ |
|---|---|---|
| − | − | 5.9 ± 0.8 (7) |
| + | − | 9.2 ± 1.1 (5) |
| + | + | 6.4 ± 0.5 (5) |

TABLE B

| Infection of virus | Administration of medicament | Splenic cells/(mice) ×10⁷ |
|---|---|---|
| − | − | 16.6 ± 1.2 (11) |
| + | − | 27.2 ± 0.6 (13) |
| + | FTS 10 μg | 14.0 ± 1.5 (7) |
| + | FTS 1 μg | 17.8 ± 1.0 (7) |
| + | FTS 0.1 μg | 28.2 ± 1.5 (6) |

This data show the amounts of splenic cells recovered from spleen of new-born ICR mice used in Jerne plaque assay.

The administration of FTS was made 2 weeks after the infection in case of the experiment in TABLE A and after 4 weeks after the infection in case of the experiment in TABLE B, the number of splenic cells is larger in TABLE B. Increase in the number of splenic cells can by the infection of virus is obviously suppressed by FTS and the number is decreased to the normal state.

EXPERIMENTAL EXAMPLE 8 Toxicity test

No toxicity was observed when 50 mg/kg and 100 mg/kg of the effective ingredient were subcutaneously administered for consecutive 14 days to a group of five ddy male mice of 5 weeks old.

EXPERIMENTAL EXAMPLE 9 Toxicity test

No toxicity was observed when 30 mg/kg of the effective ingredient was subcutaneously administered for consecutive 21 days to a group of ten wister rats of 5 weeks old.

EXPERIMENTAL EXAMPLE 10

Using cats believed to be infected with feline immunodeficiency virus (FIV), 200–500 μg/cat of FTS was administered to cats once a week for continuously more than one month and the effect of FTS was traced by a blood biochemical examination. The condition of disease was improved in view of the examination data and a result of observation of symptoms.

The medicament of this invention has effects of relieving immune inhibition caused by the infection of the above mentioned various viruses and of restoring the condition to the normal state. The medicament prevent diabetes caused by the infection of virus, and so some possibility of using this medicament as an antidiabetic agent is expected. As the medicament is effective to viruses attacking respiratory organs, digestive organs and cerebronervous organs, the use of the medicament is expected for prevention and remedy of intractable diseases of digestive organs such as idiopathic ulcerative colitis, Crohn disease and hepatitis, encephilitis, diseases caused by the infection of retrovirus, human T-cell leukemia, and AIDS. The nonapeptide (FTS) used in the medicament of this invention is a peptide originating from animals and is a natural substance. Accordingly, it is quite non-toxic in living body and has no problem of antigenicity or anaphylactic shock, unlike the case of FTS analogs having a similar amino acid configuration.

Thus, the medicament concerned with the present invention can be used as safe and useful medical preparations and veterinary medical preparations.

We claim:

1. A method of treating a vital infection in an animal consisting essentially of administering to the animal an anti-viral effective amount of a nonapeptide devoid of zinc and having the amino acid sequence:

pGlu-Ala-Lys-Ser-Gln-Gly-Gly-Ser-Asn or an ester and an amide at the carboxyl group of the C-terminal of the asparagine or a pharmacologically acceptable salt thereof, wherein the viral infection is caused by a virus causing diabetes, a digestive disorder, a respiratory disorder or a cerebronervous disorder, and said virus is selected from the group consisting of REO virus, pig Aujeszky's disease virus, hepatitis virus, human T-lymphocyte virus type I, human T-lymphocyte virus type II and human T-lymphocyte virus type III.

2. The method according to claim 1, wherein the digestive disorder is hepatitis.

3. The method according to claim 1, wherein the virus is REO virus.

4. The method according to claim 1, wherein the virus is pig Aujeszky's disease virus.

5. The method according to claim 1, wherein the virus is hepatitis virus.

6. The method according to claim 1, wherein the virus is human T-lymphocyte virus type I.

7. The method according to claim 1, wherein the virus is human T-lymphocyte virus type II.

8. The method according to claim 1, wherein the virus is human T-lymphocyte virus type III.

* * * * *